United States Patent [19]

Bordás et al.

[11] Patent Number: 4,695,309

[45] Date of Patent: Sep. 22, 1987

[54] COMPOSITION FOR PROLONGING THE ACTION OF HERBICIDES AND HERBICIDE COMPOSITIONS WITH A PROLONGED ACTION

[75] Inventors: Barna Bordás; Antal Gimesi; Magda Kovács, née Kálmán; Éva János; György Matolcsy; Márton Tüske, all of Budapest, Hungary

[73] Assignee: Eszakmagyarorszagi Vegyimuvek, Sajobabony, Hungary

[21] Appl. No.: 840,425

[22] Filed: Mar. 17, 1986

Related U.S. Application Data

[62] Division of Ser. No. 744,513, Jun. 13, 1985.

[30] Foreign Application Priority Data

Jun. 14, 1984 [HU] Hungary ............................ 2306/84

[51] Int. Cl.[4] ............................................ A01N 25/22

[52] U.S. Cl. .......................................... 71/88; 71/94; 71/95; 71/100; 71/121

[58] Field of Search ..................... 71/100, 121, 88, 94, 71/95

[56] References Cited

U.S. PATENT DOCUMENTS 2,791,605 5/1957 Dorman et al. ...................... 71/101

FOREIGN PATENT DOCUMENTS 338382 5/1982 Hungary .

OTHER PUBLICATIONS

Rehn et al., Chem. Abst., vol. 89, (1978), 48929z.

*Primary Examiner*—Catherine L. Mills

*Attorney, Agent, or Firm*—Karl F. Ross; Herbert Dubno; Jonathan Myers

[57] ABSTRACT

The invention relates to compositions (extenders) useful for prolonging the action of herbicides containing thiolcarbamate derivatives as active ingredients as well as to herbicide compositions with a prolonged action containing thiolcarbamate derivatives as active ingredients and optionally an antidote which comprises a diaminomethane derivative of the general formula (III)

$$\begin{matrix} R & & & & R \\ & \diagdown & & \diagup & \\ & & N-CH_2-N & & \\ & \diagup & & \diagdown & \\ R & & & & R \end{matrix} \qquad (III)$$

wherein the

R substituents stand independently from one another for $C_{1-6}$ alkyl groups or for $C_{2-4}$ alkenyl groups optionally substituted by a $C_{1-4}$ aklyl group;

and a process for prolonging the action of herbicide compositions containing a thiolcarbamate derivative and optionally an antidote, which comprises applying the above mentioned composition in a quantity providing the prolonged action simultaneously with or after the application of the herbicide composition.

14 Claims, No Drawings

COMPOSITION FOR PROLONGING THE ACTION OF HERBICIDES AND HERBICIDE COMPOSITIONS WITH A PROLONGED ACTION

This is a division of co-pending application Ser. No. 744,513 filed on June 13, 1985.

FIELD OF THE INVENTION

The invention relates to compositions (extenders) useful for prolonging the action of herbicides containing thiolcarbamate derivatives as active ingredients as well as to herbicide compositions with a prolonged action containing thiolcarbamate derivatives as active ingredients and optionally an antidote, namely which comprises in that for establishing the diaminomethane derivatives of the formula (III),

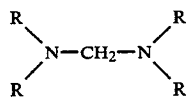

(III)

wherein the

R substituents stand independently from one another for $C_{1-6}$ alkyl groups or for $C_{2-4}$ alkenyl groups optionally substituted by a $C_{1-4}$ alkyl group.

The alkyl group preferably contains 1 to 4 carbon atoms. Preferred alkyl groups are e.g. methyl, ethyl, propyl, isopropyl, butyl, isobutyl or tertiary butyl.

A preferred alkenyl group is the allyl (2-propenyl) group.

Preferred diaminomethanes of the formula (III) are those which contain at least two allyl groups, particularly the N,N'-diallyl derivatives. The N,N'-dialkyl-N,N'-diallyldiaminomethanes are most advantageous.

BACKGROUND OF THE INVENTION

Thiolcarbamate derivatives are widely used in agricultural practice as active ingredients of effective herbicides. Thiolcarbamates and herbicide compositions containing those are reported e.g. in the U.S. Pat. Nos. 2,913,327 and 3,175,8987. Out of these compounds, S-ethyl N,N-dipropylthiolcarbamate (EPTC), S-propyl N,N-dipropylthiolcarbamate (vernolate) and S-ethyl N,N-diisobutylthiolcarbamate (butylate) are widely used in the agricultural practice.

However, in addition to the outstanding herbicidal effect, the thiolcarbamates may damage the useful cultivated plants. To prevent this effect they are frequently combined with antidotes (protecting agents). Antidotes, useful against the damaging and particularly the maize-damaging effect of herbicide compositions containing thiolcarbamate derivatives, are disclosed e.g. in the Belgian Pat. Nos. 782,120 and 806,038, in the U.S. Pat. Nos. 3,893,838 and 3,931,313 as well as in the Hungarian Pat. Nos. 165,736, 176,784 and 168,977. Out of the antidotes, N,N-diallyldichloroacetamide, reported in the Hungarian Pat. No. 165,736 has most widely been used in the agricultural practice.

By using antidotes, an appropriate selectivity is associated with the excellent herbicidal activity of the compositions containing thiolcarbamate derivatives. Concerning the possibilities for utilizing antidotes, the special literature and particularly the above-cited patent specifications are to be mentioned.

In addition to the advantageous herbicidal activity and appropriate selectivity, also the optimum duration of the activity represents a further important requirement to herbicides.

Herbicide compositions containing thiolcarbamate derivatives are in most cases sprayed on the soil surface before sowing. The concentration of the thiolcarbamate derivatives is high in the upper layer of the soil, thus the herbicidal effect is most intense just after spraying. However, the concentration of the thiolcarbamate derivatives rapidly decreases in the soil because of a number of factors, whereby after a few days they are practically undetectable.

One reason for this concentration decrease is the volatility of the active ingredients. This can be avoided by embedding the herbicide to a depth of 5 cm in the soil after having sprayed them upon the soil surface.

Another reason for the losses is the rapid decomposition of the thiolcarbamate derivatives in the soil caused by microbial and physico-chemical factors. This decomposition appears to be more rapid in fields, where thiolcarbamate-type herbicides have earlier and repeatedly been applied.

The rapid decomposition of thiolcarbamates in the soil can be prolonged by using so-called extenders, whereby the herbicidal activity and duration of the activity of the thiolcarbamates are significantly enhanced. Thus weed control becomes more effective and economical than earlier.

Herbicide compositions containing also extenders are reported in the published Hungarian patent application Nos. 783/82 and 3383/82. According to the former patent application, in addition to the thiolcarbamate active ingredients various substituted 4-phenyl-1,2,3-thiadiazole derivatives are applied on the soil, while according to the latter patent application tertiary amines, e.g. diallylamine are used. The rate of decomposition of the thiolcarbamate derivatives is significantly diminished by the use of the above compounds to result in a prolonged action.

According to the methods known in the art, the extenders are used in an amount of 2 to 4 ppm as calculated for the soil.

It is an important requirement, that the extenders used in the practice should be simply producible and cheap. Further on, these extenders should act in low doses and should effectively promote the action of the thiolcarbamates. However, the extenders known so far do not completely satisfy these practical requirements.

GENERAL DESCRIPTION OF THE INVENTION

Investigating for extenders more easily produced and more effective than the known ones, we have found that the above-mentioned extender requirements are more completely satisfied by the diaminomethanes of the formula (III) than by the extenders of the prior art.

The diaminomethane derivatives of the formula (III) are prepared in a way known in the art. In the process 1 mole equivalent of a secondary amine of the formula $$R_2NH$$

wherein R is as defined above—is reacted with 0.5 mole equivalent of formaldehyde as an aqueous solution. The product obtained is separated from the aqueous phase, dried and optionally distilled. The crude product obtained after drying is suitable to practical purposes, too.

SPECIFIC DESCRIPTION

The preparation of the compounds of the formula (III) is illustrated in details by the following Examples. The known N,N,N',N'-tetraallyldiaminomethane can be prepared e.g. by using a process disclosed in the literature [J. Am. Chem. Soc. 78, 483 (1956); Chem. Abstr. 50, 13040 (1956)] as follows.

TABLE I

| | Extender | | | Boiling point of the starting |
|---|---|---|---|---|
| Sign | Chemical name | Boiling point | Refractive index | amine at 101.325 kPa |
| A | N,N,N',N'—Tetraallyldiaminomethane | 96–98° C./2 kPa | $n_D^{24}$ = 1.4670 | 111° C. |
| B | N,N'—Diethyl-N,N'—diallyldiaminomethane | 78–80° C./2 kPa | $n_D^{20}$ = 1.4431 | 82–84° C. |
| C | N,N'—Di(n-propyl)-N,N'—diallyldiaminomethane | 114° C./2.15 kPa | $n_D^{20}$ = 1.4501 | 110–114° C. |
| D | N,N'—Diisopropyl-N,N'—diallyldiaminomethane | 105–107° C./2.68 kPa | $n_D^{20}$ = 1.4430 | 96–97° C. |
| E | N,N'—Diisobutyl-N,N'—diallyldiaminomethane | 122–123° C./2.41 kPa | $n_D^{20}$ = 1.4481 | 123° C. |
| F | N,N'—Diallyl-N,N'—di(2-methylallyl)-diaminomethane | 124–126° C./2 kPa | $n_D^{20}$ = 1.4703 | 129° C. |

EXAMPLE 1

Preparation of N,N,N',N'-tetraallyldiaminomethane

Diallylamine (97.2 g, 122.4 ml, 1 mole) is weighed in a 250 ml round-bottomed flask equipped with a mechanical stirrer, reflux condenser, thermometer and dropping funnel. Aqueous formaldehyde solution (40.5 ml, 37% by weight, 0.5 mole) is slowly added while stirring at such a rate that the temperature is maintained below 50° C. After the addition was completed, the mixture is stirred while heating in a water bath for 2 hours, then cooled, separated from the aquous phase and dried over anhydrous sodium sulphate to give 100.1 g (97.0%) of a dried crude product, the distillation of which results in 97 g (94.5%) of the pure compound named, b.p. 96°–98° C./2 kPa, $n_d^{24}$=1.4670 ($n_D^{25}$=1.4668 according to the literature).

EXAMPLE 2

Preparation of N,N'-diallyl-N,N'-diethyldiaminomethane

Ethylallylamine (85.0 g, 1 mole) is weighed in a 250 ml round-bottomed flask equipped with a mechanical stirrer, reflux condenser, thermometer and dropping funnel. Aqueous formaldehyde solution (40.5 ml, 37% by weight, 0.5 mole) is added while stirring the mixture at such a rate that the temperature is maintained below 60° C. After addition, the mixture is stirred while heating in a water bath for 2 hours, then cooled, separated from the aqueous phase and dried over anhydrous sodium sulphate to give 89 g (98%) of a dried crude product, the distillation of which results in 83.7 g (92%) of the pure title compound as a colourless liquid, b.p. 78°–80° C./2 kPa, $n_D^{20}$=1.4431.

The diaminomethanes of the formula (III) prepared in an analogous way to that described in Examples 1 and 2 as well as their physical properties (boiling point and refractive index) are shown in Table I.

The secondary amines used as starting materials for preparing the diaminomethanes of the formula (III) are known and commercially available or can be prepared by using processes known in the art. Thus, e.g. ethylallylamine can be prepared by reacting allylamine with ethyl chloride [J. Am. Chem. Soc. 65, 676 (1943)].

The extenders reported in the published Hungarian patent application No. 783/82 contain substituted 4-phenyl-1,2,3-thiadiazole derivatives requiring a synthesis of high level involving complicated intermediates as starting materials, accordingly, this type of extenders is rather expensive. E.g. the last step of the synthesis of the 4-[2'-N-(3''-trifluoromethylphenyl)-carbamoyloxyphenyl]-1,2,3-thiadiazole, according to the above published application, involves the reaction of 4-(2'-hydroxyphenyl)-1,2,3-thiadiazole with 3-trifluoromethyl isocyanate under anhydrous conditions in the presence of triethylamine in dichloromethane as solvent.

The diaminomethanes of the invention can be prepared from known, simple amines, a number of which are commercially available. The process of preparing the diaminomethanes of the invention, involves a one-step condensation reaction and is extremely simple from the technological point of view and gives high yields. The aqueous formaldehyde solution used in the process is a cheap industrially produced material.

The most effective extenders described in the published Hungarian patent application No. 3383/82 (i.e. diallyl- and alkylallylamines) are even more volatile than the volatile EPTC which latter has a short activity duration. Thus, the former extenders have a short duration, too. The boiling point of e.g. ethylallylamine is 82° to 84° C. and that of EPTC is 232° C. at atmospheric pressure.

Oppositely, the boiling points of the diaminomethane derivatives of the invention are much higher than those of the appropriately substituted known secondary amines. According to the data of Table I, the boiling points of the diaminomethanes of the invention are about the same at 2 to 2.7 kPa pressure as those of the appropriate secondary amines at atmospheric pressure. When related to atmospheric pressure, this means that the boiling points of the diaminomethane derivatives of the invention are by about 100° C. higher than those of the corresponding secondary amines. Thus, the danger of the evaporation of the extender from the upper 5 cm layer of the soil within too short a period is practically avoided, whereby the desired effect can be achieved.

The diaminomethanes of the formula (III) of the invention are suitable to prolong the action of herbicide compositions containing thiolcarbamate derivatives, particularly of those containing the thiolcarbamates of the formula (I) as active ingredients

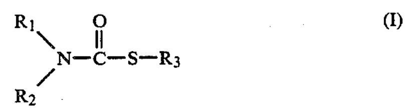

(I)

wherein

- $R_1$, $R_2$ and $R_3$ stand independently from one another for a $C_{1-4}$ alkyl group; or
- $R_1$ or $R^2$ may stand for a $C_{4-6}$ cycloalkyl group; or
- $R_1$ and $R_2$ together may represent a saturated ring containing 5 to 7 members.

The herbicide compositions containing the thiolcarbamate derivatives as active ingredients may also contain an antidote (protecting agent) for enhancing the selectivity. The suitable antidotes of the compositions containing thiolcarbamates, particularly the thiolcarbamates of the formula (I) as active ingredients are preferably the dichloroacetamide derivatives of the formula (II)

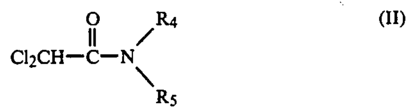

(II)

wherein

- $R_4$ and $R_5$ stand independently from one another for a $C_{2-4}$ alkenyl group, a ($C_{1-4}$ alkoxy)-($C_{1-4}$ alkoxy)-($C_{1-4}$ alkyl) group or a ($C_{2-4}$ alkenyl)-aminocarbonyl-($C_{1-4}$ alkyl) group; or
- $R_4$ and $R_5$ together may optionally represent a saturated ring consisting of 4 to 7 members optionally broken by an oxygen atom and optionally substituted at most by three methyl groups or $C_{4-6}$ cycloalkyl groups.

2-Methyl-2-dichloromethyldioxolane and 1,8-naphthalenedicarboxylic acid anhydride may also be used as preferable antidotes.

The extenders of the invention are particularly preferable for prolonging the duration of the activity of herbicide compositions containing S-ethyl N,N-di(n-propyl)-thiolcarbamate, S-(n-propyl) N,N-di(n-propyl)-thiolcarbamate, S-ethyl N,N-diisobutylthiolcarbamate, S-ethyl N,N-hexamethylenethiolcarbamate, S-ethyl N-ethyl-N-cyclohexylthiolcarbamate or S-propyl N-ethyl-N-butylthiolcarbamate as active ingredients, optionally together with antidotes. The necessity and success of using extenders are not influenced by the presence of the antidotes employed for enhancing the selectivity of compositions containing thiolcarbamate active ingredients. The most advantageous antidotes are N,N-diallyldichloroacetamide, N-allyl-N-(ethoxyethoxymethyl)-dichloroacetamide, 2,2,5-trimethyl-N-dichloroacetyloxazolidine, N,N-hexamethylenedichloroacetamide, 2-cyclohexyl-3-dichloroacetyloxazolidine, N-allyl-N-dichloroacetylglycine allylamide, 2-methyl-2-dichloromethyldioxolane and 1,8-naphthalenedicarboxylic acid anhydride.

The extender compositions of the invention and the compositions containing thiolcarbamate derivatives and antidotes can be used together as a mixture or separately after each other and applied to the soil particularly in the period of the shooting.

When applied consecutively, care should be taken that the period from the application of the extender composition up to that of the herbicide composition should be as short as possible.

The mass ratio of the extender to the thiolcarbamate active ingredient of the herbicide composition may be varied between wide limits. This ratio depends on the physical and chemical properties of the extender and of the thiolcarbamate derivative as well as on the cultivated plant, on the weeds, on the properties of the soil and further on such factors which are well known to or can easily be stated by one skilled in the art.

In the compositions of the invention, the mass ratio of the herbicide active ingredient to the extender is in general from 25:1 to 1:1, suitably from 10:1 to 4:1, preferably it is 6:1.

The used amount of the extender mainly depends on the thiolcarbamate-decomposing capacity of the soil; this amount may be 0.2 to 10 kg/hectare, suitably 0.5 to 5 kg/hectare, preferably 1 to 2 kg/hectare.

The herbicide compositions of the invention may contain the herbicidally active ingredient and the extender in the ratio defined above. The ratio of the herbicidally active ingredient to the antidote used is not different from the ratios known and usual in the practice. The total active ingredient content may vary in general from 0.1 to 95% by mass, preferably from 1 to 90% by mass. Of course these compositions include the highly concentrated ones as well as the compositions ready to use prepared from the concentrates by dilution. The compositions, mixed e.g. in a tank or in a spraying equipment just before the use from a herbicide composition optionally containing an antidote and an extender composition and optionally diluted, are also within the scope of the invention. The active ingredient content of the compositions containing only the extender separately can vary from 0.1 to 95% by mass, preferably from 1 to 90% by mass.

The composition of the invention may be any of the solid or liquid compositions acceptable in the agricultural practice, the preparation and use of which is made possible by the physical and chemical properties of the active ingredients. The compositions contain the active ingredients together with an agriculturally acceptable solid or liquid carrier as well as with surface-active additives.

The compositions may also contain other additives advantageously influencing the exertion of the effect, diminishing the volatility of the active ingredients or making easier the application. Such additives are e.g. the protective colloids, thickening agents, adhesive agents, stabilizers, solid carriers of high adsorptive capacity, such as starch, etc. In addition to the amount of the active ingredients defined above, the compositions of the invention in general contain 1 to 99% by mass of a solid or liquid carrier and optionally 0.1 to 25% by mass of a surfactant.

Any organic or inorganic, agriculturally acceptable material of natural or artificial origin can be used as carrier, such as clay, natural or artificial silicates, silicic acid, dolomite, kaolin, diatomaceous earth, grist of plant products, starch and the like as solid carriers; water, alcohols, esters, ketones, mineral oil fractions, aromatic, aliphatic or cyclic hydrocarbons, halogenated hydrocarbons, dimethylformamide, dimethylsulphoxide, N-methylpyrrolidone and the like as liquid carriers.

The surfactant may be an emulsifying, dispersing or wetting agent of either ionic and/or nonionic type. Examples of these additives are the salts of ligninsulphonic acid, phenolsulphonic acid and naphthalenesulphonic acid; the polycondensation products of ethylene oxide with fatty alcohols, fatty acids or fatty acid amides; alkyl aryl sulphonates, substituted phenols such as alkylphenols and arylphenols and polyoxyethylated phenols.

Concerning the useful surfactants known sources of the literature, e.g. the appropriate chapters of "Surfactant Science Series", Ed. Marcel Dekker, Inc., New York, are referred to. Usually, when the active ingredient or ingredients are insoluble in water and water is used as auxiliary material e.g. for dilution, the presence of at least one surfactant additive is necessary.

The solid compositions of the invention may be powders, dusts or granulates. The liquid compositions, i.e. the compositions used in a liquid form may be solutions, emulsifiable concentrates, emulsions, concentrated suspensions, wettable powders, spraying powders or pastes. The concentrated compositions can adequately be diluted. The compositions are prepared in a known manner.

The compositions of the invention may be used together with other plant protecting agents, such as herbicides, pesticides, fungicides, bactericides and plant growth regulators. In general, each plant protecting agent is suitable to the combined use which is compatible with the thiolcarbamate derivatives.

The invention also relates to a process for plant protection, the main point of which consists in that the plants or the soil sowed with seeds are treated either simultaneously or consecutively with a herbicide composition containing a thiolcarbamate derivative(s) and with the extender composition of the invention, optionally in the presence of an antidote. This treatment can be accomplished by using a composition containing the thiolcarbamate active ingredient and the extender and optionally an antidote. The active ingredients are used in a quantity suitable to achieve an effective weed control.

The applicaion of the compositions, optionally in an adequately diluted form, can be accomplished by the usual methods and equipments, e.g. by spraying, atomization, dusting, spreading and the like.

Specific Examples

The following Examples illustrate the ingredients and the preparation of some of the characteristic representatives of the compositions containing the plant protecting agents of the invention and an antidote without any limitation of the invention.

EXAMPLE I

Preparation of an emulsifiable concentrate

S-ethyl N,N-di(n-propyl)-thiolcarbamate (40 parts by mass) is mixed with N,N,N',N'-tetrallyldiaminomethane extender [8 parts by mass; compound (A)], and with oxyethylated anhydrosorbitol monostearate (1 part by mass; Tween 60) and xylene (51 parts by mass) is added to give a concentrate. with an active ingredient content of 48% by mass and containing an 5:1 mass ratio of the herbicide active ingredient to the extender. This concentrate can easily be transferred and stored and if diluted with water before use, it can be applied as a stable sprayable emulsion.

EXAMPLE II

Preparation of an emulsifiable concentrate

S-ethyl N,N-di(n-propyl)-thiolcarbamate (20 parts by mass) are dissolved in xylene (47 parts by mass) and then N,N'-diethyl-N,N'-diallyldiaminomethane [1 part by mass; compound (B)] and a polyoxyethylene fatty acid ester (2 parts by mass) are added. The total active ingredient content of this composition is 28.6% by mass, while the mass ratio of the herbicidal active ingredient to the extender is 20:1.

EXAMPLE III

Preparation of a concentrate

N,N,N',N'-Tetraallyldiaminomethane extender [95 parts by mass; compound (A)] is mixed with Tween 60 emulsifying agent (5 parts by mass) to give a concentrate with an extender content of 95% by mass.

EXAMPLE IV

Preparation of wettable powder

A mixture of S-ethyl N,N-di(n-propyl)-thiolcarbamate (10 parts by mass), N,N'-dipropyl-N,N'-diallyldiaminomethane extender (1 part by mass), cethyl polyglycol ether (1 part by mass) and kaolin (88 parts by mass) is ground in a ball mill. The total active ingredient content of the wettable powder obtained is 11% by mass, while the mass ratio of the herbicidally active ingredient to the extender is 10:1.

This wettable powder can be applied by spraying after being suspended in an appropriate amount of water.

EXAMPLE V

Preparation of an emulsifiable concentrate

A mixture containing S-ethyl N,N-di(n-propyl)-thiolcarbamate (70 parts by mass), N,N'-dipropyl-N,N'-diallyldiaminomethane as extender [12 parts by mass; compound (C)] and N,N-diallyldichloroacetamide as antidote (6 parts by mass) is dissolved in the mixture of Tween 60 (5 parts by mass) and xylene (27 parts by mass). After diluting the obtained emulsifiable concentrate with an appropriate amount of water, a stable emulsion is obtained which is suitable for spraying the surface to be treated.

EXAMPLE VI

Preparation of a granulate

N,N,N',N'-Tetraallyldiaminomethane extender (10 parts by mass) is mixed with epichlorohydrin (2.5 parts by mass) and the mixture obtained is dissolved in acetone (70 parts by mass). To this solution cetyl polyglycol ether (2.5 parts by mass) and polyethyleneglycol (35 parts by mass) are added. The solution obtained is sprayed to kaolin (950 parts by mass, particle size 0.5–0.9 mm) and the acetone is evaporated under reduced pressure to give a granulate containing 1% by mass of the extender, which can be applied by spreading to the surface to be treated.

By using similar methods to those described in the above Examples, a suitable composition can be prepared from any of the extenders listed in Table I, optionally by employing one or more thiolcarbamate derivative(s) and/or antidote(s). A composition can also be made containing the extender alone or in an admixture with the appropriate additives.

The capacity of extenders of the invention to prolong the decomposition of thiolcarbamate derivatives in the soil was studied in laboratory experiments.

The biological effects of the herbicide compositions containing an extender of the invention, thiolcarbamate derivative and optionally an antidote were studied in greenhouse tests on the following plants: maize (*Zea mays*), barley (*Hordeum vulgare*), wild oat (*Avena fatua*), barnyard grass (*Echinocloa crus-galli*), millet (*Setaria glauca*), white mustard (*Sinapis alba*) and pilous amaranth (*Amaranthus retroflexus*).

It has been stated on the basis of these laboratory experiments that the extenders of the invention effectively delay the decomposition of thiolcarbamate derivatives in the soil and are superior to the known extenders.

In the greenhouse tests it has been observed that the herbicide compositions containing the extenders of the invention together with a thiolcarbamate derivative(s) and optionally an antidote(s) have a more intense herbicidal action than the similar compositions containing no extender and exceed the herbicidal effect of the compositions containing any known extender.

The activity of the extenders of the invention is illustrated in the following Examples. The Examples are not limiting.

EXAMPLE A

100–100 g air-dried, pre-tested soil was placed in Erlenmeyer flasks of 250 ml volume. An 1.39 ml volume of the commercially available Eptam 6E herbicide (EPTC) was mixed with 1 liter of distilled water. An 0.6 ml volume of the emulsion obtained was added to 5 ml of water and the emulsion was poured onto the 100 g of soil. [The commercially available Eptam 6E contained 0.82 kg/liter of S-ethyl N,N-di(n-propyl)-thiolcarbamate as active ingredient.] The above operation was adequate to a treatment with 6 ppm of the thiolcarbamate as calculated for the soil. Subsequently, 0.5–0.5 ml of xylene was added to 1.05 g samples of the emulsifiable concentrates prepared according to Example III containing the extenders of invention or diallylamine, respectively, the latter used as control, whereupon each of the solutions thus prepared was suspended in 1 liter of water. From the emulsions obtained like this 0.4 ml was added to each of the soil samples previously treated with the thiolcarbamate derivative. This treatment was adequate to a 4 ppm dose of the extender as calculated for the soil. Then water was added to the soil in an amount providing the appropriate humidity but avoiding the sticking together. (30 ml of water was required for one flask). The soil in the flasks was thoroughly mixed by using a glass rod, the flasks were closed with cotton-wool providing the aerobic conditions and then thermostated (incubated) at 25° C. in the dark for 4 days.

After the incubation, 100 ml of water and 50 ml of toluene were added to each of the soil samples, whereupon the suspension was mechanically stirred at a high revolution rate for 10 minutes and then let stay for separating the organic phase. The thiolcarbamate content of the toluene phase was analyzed by using gas chromatography. The results of this determination were converted to the quantity of the thiolcarbamate active ingredient as calculated for the soil and expressed in ppm. The results of the persistence measured in the soil are shown in Table II.

TABLE II

Herbicide: S—Ethyl N,N—di(n-propyl)-thiolcarbamate (EPTC) in a 6 ppm dose as calculated for the soil
Extender: in a 4 ppm dose as calculated for the soil
Duration of the experiment: 4 days at 25° C.

| Extenders of the invention | EPTC content (ppm) | Secondary amine extenders | EPTC content (ppm) |
|---|---|---|---|
| A | 4.15 | Diallylamine | 3.58 |
| B | 3.87 | Ethylallylamine | 3.00 |
| C | 3.49 | Propylallylamine | 2.60 |
| D | 3.21 | Isopropylallylamine | 2.65 |
| E | 4.18 | Isobutylallylamine | 3.52 |
| F | 3.35 | Allyl-(2-methylallyl)-amine | 2.20 |
| Control (without extender)* | Undetectable | | Undetectable |

*Note:
Within this experiment, the detectability limit of EPTC was 0.05 ppm.

It can be stated on the basis of the results shown in Table II that the diaminomethane derivatives of the invention inhibited the decomposition of EPTC to a higher extent than did the most preferable secondary amines described in the published Hungarian patent application No. 3383/82.

Based on the similar experimental conditions, the results shown in Table II may be compared to the activity of the extenders reported in either the published Hungarian patent application No. 3383/82 or No. 783/82. According to the latter patent application, on using the most active 4-[2′-N-(3″-trifluoromethylphenyl)-carbamoyloxyphenyl]-1,2,3-thiadiazole as extender under identical experimental conditions, the concentration of EPTC was detected to be 2.37 ppm after 4 days thus, it was inferior to the extenders of this invention.

EXAMPLE B

Under identical conditions with those described in Example A, the dose of EPTC was kept unchanged while N,N,N′,N′-tetraallyldiaminomethane was used as extender in gradually decreasing (halved) doses. Diallylamine, a known extender was used as control. The results are shown in Table III.

TABLE III

Herbicide: S—Ethyl N,N—di(n-propyl)-thiolcarbamate (EPTC) in a 6 ppm dose as calculated for the soil
Extender: N,N,N′,N′—Tetraallyldiaminomethane or diallylamine, respectively, in doses decreasing gradually from 2 ppm to 0.25 ppm
Duration of the experiment: 4 days at 25° C.

| Starting concentration of the extenders (ppm) | EPTC concentration measured in the presence of extender (A) after 4 days ppm | EPTC concentration measured in the presence of diallylamine as extender after 4 days ppm |
|---|---|---|
| 2 | 3.8 | 2.9 |
| 1 | 3.7 | 2.9 |
| 0.5 | 3.7 | 1.4 |

TABLE III-continued

Herbicide: S—Ethyl N,N—di(n-propyl)-thiolcarbamate (EPTC) in a 6 ppm dose as calculated for the soil
Extender: N,N,N',N'—Tetraallyldiaminomethane or diallylamine, respectively, in doses decreasing gradually from 2 ppm to 0.25 ppm
Duration of the experiment: 4 days at 25° C.

| Starting concentration of the extenders (ppm) | EPTC concentration measured in the presence of extender (A) after 4 days ppm | EPTC concentration measured in the presence of diallylamine as extender after 4 days ppm |
|---|---|---|
| 0.25 | 2.4 | Undetectable* |

*Note:
Within this experiment, the detectability limit of EPTC was 0.05 ppm.

It is obvious from the results shown in Table III that the decomposition of EPTC in the soil was effectively inhibited by N,N,N',N'-tetraallyldiaminomethane used as extender even in such a dose which is inactive in the case of diallylamine.

It has been shown by the practical experiences that the decomposition of thiolcarbamates is much more rapid in soils previously treated with thiolcarbamate derivatives than is in untreated soils. Thus, the soil required to the experiments was pre-treated in the following way.

Pre-treatment of a soil with S-ethyl N,N-di(n-propyl)-thiolcarbamate

Unsterilized vegetable soil (with an organic material content of 2.2 to 2.5 g/100 g and a pH value of 6.5) was placed up to 10 cm thickness in plastic dishes of 30×30 cm dimension. Three ranks of maize (10 seeds each) and two ranks of millet (Setaria glauca; 25 seeds each) were sown into the thickened and levelled soil in a depth of 1.5 cm. Immediately after sowing 45 microliters of Eptam 6E herbicide emulsified in 50 ml of water was sprayed to the soil surface on each of the dishes. This treatment was equal to the application of 5 liters of composition/hectare in the usual practice. The dishes were kept in a greenhouse at 20° to 25° C. and sprinkled as needed for 21 days. The sprinkling was stopped on the 22nd day and the plants were removed together with their root-system on the 28th days. The soil was taken out and sifted as air-dry. The air-dry soil free of the plant residues was used as a "pre-treated soil" for the further investigations.

EXAMPLE C

Investigation of the herbicidal activity of the compositions of the invention in a pre-treated soil The pre-treated soil was placed up to 8 cm thickness in plastic dishes of 50×35 cm dimension, thickened, then the seeds of the following plants were sown in ranks in a depth of 1.0 to 1.5 cm: maize, barley, wild oat, barnyard grass, millet, white mustard and pilous amarant. Then 1 ml of toluene was added to 1.25 g of a concentrate containing 80% by mass of S-ethyl N,N-di(n-propyl)thiolcarbamate and 16% by mass of the extender (A) and the emulsifiable concentrate thus prepared was mixed into 1 liter of water. A similar emulsion was prepared by using diallylamine, a known extender instead of the extender (A).

A control without any extender was prepared by emulsifying 0.7 ml of commercially available Eptam 6E herbicide in 1 liter of water.

Immediately after sowing, 100 or 50 ml, respectively, of the above emulsions were sprayed to the soil surface in each of the dishes, which was adequate to a treatment with 8.0 or 4.0 liters/hectare of Eptam 6E, respectively, as calculated for the EPTC content of the compositions. The mass ratio of the thiolcarbamate to the extender was 5:1 in the compositions employed.

The dishes were kept at 20° to 25° C. in a greenhouse and sprinkled as needed. The condition of the plants was evaluated on the 20th day by measuring the green length and by judging the appearance and state of the plants as compared to the untreated control. In Table IV the green length is given as the percentage of the untreated control, while the state of the plants is scored from 0 to 100, where 100 means a completely intact state without any damage and 0 means the total perishment of the plants. The results are shown in Table IV.

EXAMPLE D

Examination of the herbicidal activity of the compositions of the invention in a soil without pre-treatment This experiment was carried out as described in Example C except that the unsterilized soil was used without any pre-treatment, and the soil was sprayed with emulsions containing EPTC in an amount adequate to a treatment with a diminished quantity of 3.0 liters/hectare or 6.0 liters/hectare, respectively of Eptam 6E (i.e. 75 or 37.5 ml, respectively, of the above emulsions were used). The results are shown in Table V.

TABLE IV

| | Examinations in pre-treated soil | | | | | | | | | | | |
|---|---|---|---|---|---|---|---|---|---|---|---|---|
| | Dose of the herbicide: | | | | | | | | | | | |
| | 4.0 liters/hectare | | | | | | 8.0 liters/hectare | | | | | |
| | Extender: | | | | | | | | | | | |
| | — | | DAA | | (A) | | — | | DAA | | (A) | |
| | H | S | H | S | H | S | H | S | H | S | H | S |
| Maize | 100 | 100 | 100 | 100 | 100 | 100 | 90 | 100 | 80 | 60 | 80 | 70 |
| Barley | 100 | 100 | 90 | 80 | 80 | 50 | 60 | 50 | — | 0 | — | 0 |
| Wild oat | 100 | 100 | — | 0 | — | 0 | 80 | 75 | — | 0 | — | 0 |
| Barnyard grass | 100 | 100 | 60 | 30 | 50 | 30 | 80 | 50 | — | 0 | — | 0 |
| Millet | 100 | 100 | 70 | 50 | 50 | 20 | 70 | 75 | — | 0 | — | 0 |
| White mustard | 100 | 100 | 100 | 100 | 100 | 100 | 100 | 100 | 100 | 100 | 90 | 100 |

TABLE IV-continued

| | Examinations in pre-treated soil | | | | | | | | | | | |
|---|---|---|---|---|---|---|---|---|---|---|---|---|
| | Dose of the herbicide: | | | | | | | | | | | |
| | 4.0 liters/hectare | | | | | | 8.0 liters/hectare | | | | | |
| | Extender: | | | | | | | | | | | |
| | — | | DAA | | (A) | | — | | DAA | | (A) | |
| | H | S | H | S | H | S | H | S | H | S | H | S |
| Amaranth | 100 | 100 | 50 | 50 | 50 | 50 | 80 | 100 | 40 | 20 | — | 0 |

Notes:
the herbicide was S—ethyl N,N—di(n-propyl)-thiolcarbamate (0.72 kg of active ingredient in 1 liter of the composition)
DAA: Diallylamine
(A): N,N,N',N'—tetraallyldiaminomethane
H: Height as percentage of the control
S: State of the plants

TABLE V

| | Examinations in soil without pre-treatment | | | | | | | | | | | |
|---|---|---|---|---|---|---|---|---|---|---|---|---|
| | Dose of the herbicide: | | | | | | | | | | | |
| | 3.0 liters/hectare | | | | | | 6.0 liters/hectare | | | | | |
| | Extender: | | | | | | | | | | | |
| | — | | DAA | | (A) | | — | | DAA | | (A) | |
| | H | S | H | S | H | S | H | S | H | S | H | S |
| Maize | 100 | 100 | 100 | 100 | 100 | 100 | 80 | 90 | 90 | 100 | 90 | 90 |
| Barley | 100 | 100 | 70 | 80 | 80 | 90 | 70 | 90 | 20 | 10 | 50 | 30 |
| Wild oat | 20 | 5 | — | 0 | — | 0 | — | 0 | — | 0 | — | 0 |
| Barnyard grass | 40 | 20 | 30 | 20 | 20 | 10 | 30 | 10 | — | 0 | — | 0 |
| Millet | 50 | 50 | 30 | 40 | 30 | 20 | 20 | 20 | — | 0 | — | 0 |
| White mustard | 100 | 100 | 100 | 100 | 100 | 100 | 100 | 100 | 100 | 100 | 100 | 100 |
| Amaranth | 80 | 80 | 20 | 20 | 30 | 20 | 40 | 30 | — | 0 | — | 0 |

The Note and abbreviations are the same as in Table IV.

EXAMPLE E

This experiment was carried out as described in Example D except that Vernolate 72 EC [S-(n-propyl)-N,N-di(n-propyl)-thiolcarbamate] was used instead of Eptam 6E. The results are shown in Table VI.

TABLE VI

| | Examinations in soil without pre-treatment | | | | | | | | | | | |
|---|---|---|---|---|---|---|---|---|---|---|---|---|
| | Dose of the herbicide: | | | | | | | | | | | |
| | 3.0 liters/hectare | | | | | | 6.0 liters/hectare | | | | | |
| | Extender: | | | | | | | | | | | |
| | — | | DAA | | (A) | | — | | DAA | | (A) | |
| | H | S | H | S | H | S | H | S | H | S | H | S |
| Maize | 100 | 100 | 100 | 100 | 100 | 100 | 90 | 90 | 90 | 90 | 90 | 90 |
| Barley | 90 | 100 | 70 | 70 | 80 | 90 | 70 | 80 | 30 | 20 | 30 | 20 |
| Wild oat | 10 | 10 | 5 | 0 | 5 | 0 | — | 0 | — | 0 | — | 0 |
| Barnyard grass | 40 | 20 | 30 | 20 | 20 | 10 | 40 | 30 | — | 0 | — | 0 |
| Millet | 40 | 50 | 30 | 40 | 20 | 20 | 30 | 30 | 5 | 0 | — | 0 |
| White mustard | 40 | 40 | 30 | 30 | 20 | 20 | 30 | 20 | 10 | 10 | 5 | 0 |
| Amaranth | 80 | 70 | 30 | 20 | 20 | 10 | 40 | 30 | 5 | 0 | — | 0 |

Note:
the herbicide was S—(n-propyl)-N,N—di(n-propyl)-thiolcarbamate (0.72 kg of active ingredient in 1 liter of the composition
The abbreviations used in the Table VI are the same as in Table IV.

What we claim is:

1. A composition with prolonged herbicidal activity which comprises:

(a) a herbicidal compound of the Formula (I)

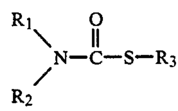

wherein $R_1$, $R_2$ and $R_3$ are each $C_1$ to $C_4$ alkyl; or $R_1$ and $R_2$ are each $C_4$ to $C_6$ cycloalkyl;

(b) an antidotal compound of the Formula (II)

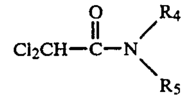

wherein $R_4$ and $R_5$ are each $C_2$ to $C_4$ alkenyl, a ($C_1$ to $C_4$ alkoxy)-($C_1$ to $C_4$ alkoxy-($C_1$ to $C_4$ alkyl) group, or a ($C_2$ to $C_4$ alkenyl)-aminocarbonyl-($C_1$ to $C_4$ akyl) group; or $R_4$ and $R_5$ together with the adjacent nitrogen atom may represent a saturated ring consisting of 4 to 7 members optionally broken by an oxygen atom and optionally substituted at most by three methyl groups or $C_4$ to $C_6$ cycloalkyl groups; and (c) an extender compound of the Formula (III)

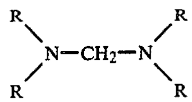

wherein the

R substituents are each independently $C_1$ to $C_6$ alkyl or $C_2$ to $C_4$ alkenyl each unsubstituted or substituted by a $C_1$ to $C_4$ alkyl group, wherein at least two of the R substituents are each allyl and wherein the weight ratio between the herbicidal compound of the formula (I) to the extender compound of the formula (III) is 25:1 to 1:1.

2. A process for prolonging the action of a thiolcarbamate herbicidal compound which comprises the step of applying to the soil together with or subsequent to the application of a thiolcarbamate herbicidal compound of the Formula (I)

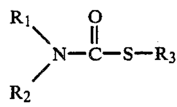

wherein $R_1$, $R_2$ and $R_3$ are each $C_1$ to $C_4$ alkyl; or $R_1$ and $R_2$ are each $C_4$ to $C_6$ cycloalkyl;

(a) an antidotal compound of the Formula (II)

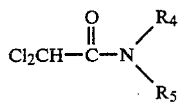

wherein $R_4$ and $R_5$ are each $C_2$ to $C_4$ alkenyl, a ($C_1$ to $C_4$ alkoxy)-($C_1$ to $C_4$ alkoxy)-($C_1$ to $C_4$ alkyl) group, or a ($C_2$ to $C_4$-alkenyl)-aminocarbonyl-($C_1$ to $C_4$ alkyl) groupl or $R_4$ and $R_5$ together with the adjacent nitrogen atom may represent a saturated ring consisting of 4 to 7 members optionally broken by an oxygen atom and optionally substituted at most by three methyl groups or $C_4$ to $C_6$ cycloalkyl groups, and (b) an extender compound of the Formula (III)

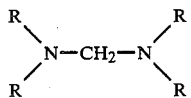

wherein the

R substituents are each independently $C_1$ to $C_6$ alkyl or $C_2$ to $C_6$ alkenyl, each unsubstituted or substituted by a $C_1$ to $C_4$ alkyl group; wherein at least two of the R substituents are each allyl and wherein the weight ratio between the herbicidal compound of the Formula (I) to the extender compound of the Formula (III) is 25:1 to 1:1.

3. A composition with prolonged herbicidal activity which comprises:

(a) a herbicidal compound of the Formula (I)

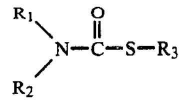

wherein $R_1$, $R_2$ and $R_3$ are each $C_1$ to $C_4$ alkyl; or $R_1$ and $R_2$ are each $C_4$ to $C_6$ cycloalkyl;

(b) an antidotal compound of the Formula (II)

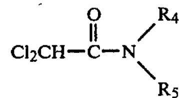

wherein $R_4$ and $R_5$ are each $C_2$ to $C_4$ alkenyl, a ($C_1$ to $C_4$ alkoxy)-($C_1$ to $C_4$ alkoxy)-$C_1$ to $C_4$ alkyl group; or a ($C_2$ to $C_4$ alkenyl)-aminocarbonyl)-($C_1$ to $C_4$ alkyl) group; or $R_4$ and $R_5$ together with the adjacent nitrogen atom may represent a saturated ring consisting of 4 to 7 members optionally broken by an oxygen atom and optionally substituted by at most three methyl groups or $C_4$ to $C_6$ cycloalkyl groups; and (c) an extender compound of the Formula (III)

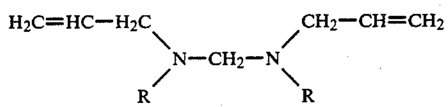

wherein the R substituents are each independently $C_1$ to $C_4$ alkyl or $C_2$ to $C_4$ alkenyl, each unsubstituted or substituted by a $C_1$ to $C_4$ alkyl group, wherein the weight ratio between the herbicidal compound of the Formula (I) to the extender compound of the Formula (III) is 25:1 to 1:1.

4. The composition as defined in claim 3 which comprises as the compound of the Formula (III): N,N,N',N'-tetraallyldiaminomethane, N,N'-diethyl-N,N'-diallyldiaminomethane, N,N'-dipropyl-N,N'-diallyldiaminomethane, N,N'-diisopropyl-N,N'-diallyldiaminomethane, N,N'-diisobutyl-N,N'-diallyldiaminomethane, or N,N'-diallyl-N,N'-di(2-methylallyl)-diaminomethane for the prolonging of the effect.

5. The composition as defined in claim 3 which comprises as the compound of the Formula (I): S-ethyl-N,N-di(n-propyl)-thiolcarbamate, S-(n-propyl)-N,N-di(n-propyl)-thiolcarbamate, S-ethyl N,N-diisobutylthiolcarbamate, S-ethyl-N,N-diisobutylthiolcarbamate, S-ethyl-N-cyclohexyl-N-ethylthiolcarbamate or S-propyl-N-butyl-N-ethyl-thiolcarbamate.

6. The composition as defined in claim 3 which comprises as the herbicidal antidote a compound of the Formula (II) which is: N,N-diallyldichloroacetamide, N-allyl-N-(ethoxyethoxymethyl)-dichloroacetamide, 2,2,5-trimethyl-N-dichloroacetyloxyzolidine, N,N-hexamethylenedichloroacetamide, 2-cyclohexyl-3-dichloro-acetyloxazolidine, N-allyl-N-dichloroacetylglycine allylamide, 2-methyl-2-dichloromethyldioxolane or 1,8 -naphthalenedicarboxylic acid anhydride.

7. The composition as defined in claim 3 which comprises as the compound of the Formula (I) S-ethyl-N,N-di(n-propyl)thiolcarbamate.

8. The composition as defined in claim 3 which comprises as the compound of the Formula (I) S-n-propyl-N,N-di(n-propyl)-thiolcarbamate.

9. A process for prolonging the action of a thiolcarbamate herbicidal compound which comprises the step of applying to the soil together with or subsequent to the application of a thiolcarbamate herbicidal compound of the Formula (I)

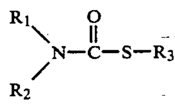

wherein $R_1$, $R_2$ and $R_3$ are each $C_1$ to $C_4$ alkyl; or $R_1$ and $R_2$ are each $C_4$ to $C_6$ cycloalkyl;

(a) an antidotal compound of the Formula (II)

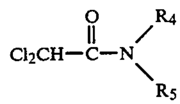

wherein $R_4$ and $R_5$ are each $C_2$ to $C_4$ alkenyl, a ($C_1$ to $C_4$ alkoxy)-($C_1$ to $C_4$ alkoxy)-$C_1$ to $C_4$ alkyl group, or a ($C_2$ to $C_4$ alkenyl)aminocarboyl-($C_1$ to $C_4$ alkyl) group; or $R_4$ and $R_5$ together with the adjacent nitrogen atom may represent a saturated ring consisting of 4 to 7 members optionally broken by an oxygen atom and optionally substituted by at most three methyl groups or $C_4$ to $C_6$ cycloalkyl groups; and (b) an extender compound of the Formula (III)

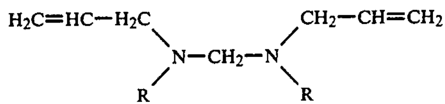

wherein the R substituents are each independently $C_1$ to $C_4$ alkyl or $C_2$ to $C_4$ alkenyl, each unsubstituted or substituted by a $C_1$ to $C_4$ alkyl group, wherein the weight ratio between the herbicidal compound of the Formula (I) to the extender compound of the Formula (III) is 25:1 to 1:1.

10. The method as defined in claim 9 which comprises as the compound of the Formula (III): N,N,N',N'-tetraallyldiaminomethane, N,N'-diethyl-N,N'-diallyldiaminomethane, N,N'-dipropyl-N,N'-diallyl-diaminomethane, N,N'-diisopropyl-N,N'-diallyldiaminomethane, N,N'-diisobutyl-N,N'-diallyldiaminomethane, or N,N'-diallyl-N,N'-di(2methylallyl)-diaminomethane for the prolonging of the effect.

11. The method as defined in claim 9 which comprises as the compound of the Formula (I): S-ethyl-N,N-di(n-propyl)-thiolcarbamate, S-(n-propyl)-N,N-di(n-propyl)-thiolcarbamate, S-ethyl N,N-diisobutylthiolcarbamate, S-ethyl-N,N-diisobutylthiolcarbamate, S-ethyl-N,N-hexamethylene-thiolcarbamate, S-ethyl-N-cyclohexyl-N-ethylthiolcarbamate or S-propyl-N-butyl-N-ethyl-thiolcarbamate.

12. The method as defined in claim 9 which comprises as the herbicidal antidote a compound of the Formula (II) which is: N,N-diallyldichloroacetamide, N-allyl-N-(ethoxyethoxymethyl)-dichloroacetamide, 2,2,5-trimethyl-N-dichloroacetyloxyzolidine, N,N-hexamethylene-dichloroacetamide, 2-cyclohexyl-3-dichloro-acetyloxazolidine, N-allyl-N-dichloroacetylglycine allylamide, 2-methyl-2-dichloromethyldioxolane or 1,8-naphthalenedicarboxylic acid anhydride.

13. The method defined in claim 9 which comprises as the compound of the Formula (I) S-ethyl-N,N-di(n-propyl)thiolcarbamate.

14. The method defined in claim 9 which comprises as the compound of the Formula (I) S-n-propyl-N,N-di(n-propyl)thiolcarbamate.

* * * * *